United States Patent
Stafford

(10) Patent No.: US 9,744,110 B2
(45) Date of Patent: Aug. 29, 2017

(54) METHOD OF TREATING CONDITIONS OF THE EYELID

(71) Applicant: Debra Louise Stafford

(72) Inventor: Vivi Robyn Stafford, Mission Viejo, CA (US)

(\*) Notice: Subject to any disclaimer, the term of this patent is extended or adjusted under 35 U.S.C. 154(b) by 0 days.

(21) Appl. No.: 14/805,459

(22) Filed: Sep. 29, 2015

(65) Prior Publication Data

US 2017/0087072 A1    Mar. 30, 2017

(51) Int. Cl.
*A61Q 19/08* (2006.01)
*A61K 8/362* (2006.01)
*A61K 31/194* (2006.01)

(52) U.S. Cl.
CPC .......... *A61K 8/362* (2013.01); *A61K 31/194* (2013.01); *A61Q 19/08* (2013.01)

(58) Field of Classification Search
None
See application file for complete search history.

(56) References Cited

U.S. PATENT DOCUMENTS 8,846,066 B2 * 9/2014 Kolodney ............... A61K 8/63
424/401

OTHER PUBLICATIONS

Bernstein et al., Dermatol. Surg. 23, 689-94 (1997).*

\* cited by examiner

*Primary Examiner* — Theodore R West
(74) *Attorney, Agent, or Firm* — Feeney Law Group; Alan F. Feeney

(57) ABSTRACT

A method for tightening the fat septa of the hypodermis of the eyelids by administering an aqueous solution of citric acid resulting in the reduction of skin tenting, skin sag, lid laxity and skin overhang of the upper and lower eye lids.

13 Claims, No Drawings

METHOD OF TREATING CONDITIONS OF THE EYELID

BACKGROUND OF THE INVENTION

This invention was not made with U.S. government support.

Overhang and tenting of the skin in the upper and lower lids of the eyes are unique phenomena that can occur in individuals that are not in advanced ages. The skin in the upper and lower lids of the eyes can be resistant to eye creams for the reduction of the presentation of skin tenting, overhang and laxity. In the case of citric acid, there are no approved or rigorously evaluated non-surgical alternatives for the upper and lower lids. Surgical alternatives include, on a scale of increasing invasiveness, various forms of surgical upper and lower lid blepharoplasties where incisions are made and fat is surgically teased out in candidates. All surgeries are associated with the known risks of anesthesia, infection, bleeding, bruising, scarring, as well as the possibility of poor outcome and the expected discomfort and "down-time" for the patient. Presently, there are no injections for the upper and lower lids that reverse skin tenting, laxity, overhang, sag or puffiness. There has been hesitation in the market to date for injections into the tissue proximal to the orbits of the eyes. Injections into this anatomical sight increase the risk of causing blindness in the patient. None of the cosmetic substances currently in the cosmetic injection market can be injected into the eye lids or the tissue proximal to the orbits of the eyes. There is a need in the market, therefore, for a non-surgical alternative to address skin conditions of the eye lids which does not pose the risk of causing blindness. A citrate solution however, could be used to successfully treat skin conditions of the eye lids without the risk of causing blindness in patients. The demand for non-surgical eye correction is very high in the cosmetic market.

In spite of procedural risks, the growing appeal of cosmetic medical treatment of said procedures is a testament to the psychological importance of body image and the beneficial outcomes of these procedures. as perceived by the patients who seek them. However, the significance of a product that corrects signs of peri-orbital aging with little to no risk is significant.

BRIEF DESCRIPTION OF THE INVENTION

The present invention is directed to a method for the non-surgical reduction of localized loose skin in the upper and lower lids that is associated with the normal aging loss of the integrity of the dermis that supports the epidermis. The upper lid tenting and overhang and lower lid tenting, overhang and laxity can give the appearance of one looking tired when not. In particular, a treatment for skin tenting, lid laxity, sag and overhang in the upper and lower lids of the eyes with an aqueous solution of citric acid with a viscosity consistent with water at 20 to 25° C.

DETAILED DESCRIPTION OF THE INVENTION

The Invention provides a method for improvement of the tired look of human skin of the eye lids comprising administering citric acid or a salt thereof to a patient in need thereof, wherein the administering is a subcutaneous injection. The method tightens subcutaneous fat via strengthening of wall proteins located in the hypodermis of the skin of the upper and lower eye lids to thereby enhance facial appearance. The injection is, for example, in the form of one or more large blebs or small boluses. The method may also include an additional step of measuring one or more improvements in the appearance of the skin with a measuring device. When the citric acid or salt thereof is placed in the superficial plane or deep plains of subdermal fat, it causes skin tightening by connective tissue contractions, increase support of the subcutaneous tissue, and tensile strength to protein strands below the dermis. The citric acid or salt thereof may be either natural or synthetic.

The compositions, treatment schedules and methods of using said compositions discovered by the inventor effectively remove the effect of tenting or impending tenting of the upper and lower lids. Generally speaking, tenting and impending tenting and tented skin ptosis of the upper and lower lids of the eyes are a well-known beauty problem and the problem can progress to impairment if treatment is delayed for reversing the presentation of the tented and hanging skin. In addition, the effect of tightening tented and hanging skin with subcutaneous injections repositions fat and re-compartmentalizes fatty tissue in its more anatomic position.

Citrate constituted with isotonic water and dextrose can stimulate elastin tensile strength below the dermis and above and below the muscle to tighten skin, decrease the appearance of aging, and contour deficiencies, fine lines and wrinkles. Citrate is found in the serum of individuals, but also can be manufactured and processed.

The composition of the instant application is based on 100 volume percent calculations. In particular, the composition of the instant application is comprised of: 10 volume percent: 3.2% sodium citrate buffer. In the preferred embodiment, approximately 0.109 ml of sodium citrate buffer is used. Citric acid, having the formula,

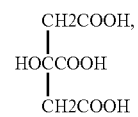

may also be used.

The 3.2% sodium citrate buffer or citric acid is combined together with 90 volume percent: 36.6% isotonic water, 45% sodium chloride and 6.4% glycerol with trace electrolytes.

In an embodiment of the present invention, sodium citrate powder, or a solution thereof, may be pre-loaded into a 20 cc intravenous vial for dispensing, and combined in an 8 to 10 cc syringe filled with a liquid volume comprising isotonic water, sodium chloride, and glycerol. The injector mixes the ingredients back and forth between two 10 cc syringes until the formula is reconstituted to a dose of 10 ml prior to administration.

The mixture should have a neutral pH prior to injection.

Applicant respectfully requests entry of the above amendments to the specification.

Applicant respectfully asserts that the proposed amendments to the specification do not introduce new matter.

The composition of the instant application for the subcutaneous reversal of skin tenting, sag, lag of the upper and/or lower lid should be administered only by competent plastic surgeons, dermatologists or other medical doctors and their eligible licensed staff. Injections into the sub-dermal fat tissue in patients having skin tenting, sag or lag of the eye lids will tighten and thicken the subdermal fat bands and the hypodermis thereby reducing the appearance of fine lines, wrinkles, and pores of the eye lids.

What is claimed is:

1. A method for improvement of the tired look of human skin comprising administering citric acid or a salt thereof to a patient in need thereof, wherein said administering is subcutaneous injection.

2. The method of claim 1, wherein said administering tightens subcutaneous fat via strengthening of wall proteins located in the hypodermis of the upper and lower eye lids to thereby enhance facial appearance.

3. The method of claim 2, wherein said method is used for cosmetic purposes.

4. The method of claim 1, wherein said injection is in the form of one or more blebs or boluses.

5. The method according to claim 4, wherein said injection is administered to the eye lids of the patient in need of treatment.

6. The method according to claim 5, wherein said patient suffers from a condition of the eye lids selected from the group consisting of skin tenting, impending skin tenting, lid laxity, skin sag, ptosis or skin overhang.

7. The method according to claim 4, wherein said injection is administered to proximal to the orbit of the eyes of the patient in need of treatment.

8. The method according to claim 4, wherein said injection is given to the patient in a 10 ml dose.

9. The method of claim 1, further comprising measuring one or more improvements in the appearance of the skin with a measuring device.

10. The method of claim 1, wherein said citric acid or salt thereof is places in the superficial plane or deep plains of subdermal fat thereby causing skin tightening by connective tissue contractions, increased support of subcutaneous tissue, and providing tensile strength to protein strands below the dermis.

11. The method of claim 1, wherein citric acid or salt thereof is obtained from natural sources is synthetic.

12. The method according to claim 1, wherein said method is administered to a patient in need thereof either before or after the patient undergoes blepharoplasty surgery of the eye lids.

13. The method according to claim 1, wherein said method results in the re-positioning of fat and/or re-compartmentalizing of fatty tissue in the eye lids of the patient undergoing said method.

* * * * *